United States Patent [19]

Pallos et al.

[11] 4,036,628
[45] July 19, 1977

[54] PHOSPHORUS CONTAINING HERBICIDE ANTIDOTES

[75] Inventors: Ferenc M. Pallos, Walnut Creek; Don R. Baker, Orinda, both of Calif.

[73] Assignee: Stauffer Chemical Company, Westport, Conn.

[21] Appl. No.: 582,944

[22] Filed: June 2, 1975

Related U.S. Application Data

[63] Continuation-in-part of Ser. No. 305,770, Nov. 13, 1972, abandoned.

[51] Int. Cl.² .......... A01N 9/36; A01N 9/00; A01N 9/12
[52] U.S. Cl. .......... 71/86; 71/88; 71/93; 71/100; 71/110; 71/117; 71/118; 71/120
[58] Field of Search .......... 71/100, 86, 88; 260/961, 963

[56] References Cited

U.S. PATENT DOCUMENTS

| | | | |
|---|---|---|---|
| 2,913,327 | 11/1959 | Tilles et al. | 71/100 |
| 3,626,037 | 12/1971 | Randall et al. | 260/961 |
| 3,705,215 | 12/1972 | Vogel et al. | 260/961 |
| 3,808,265 | 4/1974 | Randall et al. | 71/86 X |

*Primary Examiner*—Joseph Paul Brust
*Attorney, Agent, or Firm*—Harry A. Pacini

[57] ABSTRACT

Herbicidal compositions comprising an active herbicidal compound and an antidote therefor and the methods of use; the antidote compounds correspond to the phosphorus-containing compounds having the formula

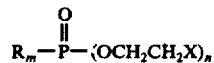

wherein R is lower alkoxy, haloalkyl or haloalkoxy, X is chlorine or bromine, $n$ is an integer from 1 to 3, inclusive, $m$ is 0 or an integer 1 or 2, provided that $n + m$ is 3.

18 Claims, No Drawings

PHOSPHORUS CONTAINING HERBICIDE ANTIDOTES

This application is a continuation-in-part application of copending Ser. No. 305,770, filed Nov. 13, 1972, now abandoned.

BACKGROUND OF THE INVENTION

Among the many herbicidal compounds commercially available, the thiocarbamates alone or admixed with other herbicides, such as the triazines, have reached a relatively high degree of commercial success. These herbicides are immediately toxic to a large number of weed pests at different concentrations varying with the resistance of the weed pests. Some examples of these compounds are described and claimed in U.S. Pat. Nos. 2,913,327, 3,037,853, 3,175,897, 3,185,720, 3,198,786 and 3,582,314.

It has been found in practice that the use of these thiocarbamates as herbicides on crops sometimes causes serious injuries to the crop plant. When used in the recommended amounts in the soil to control many broadleaf weeds and grasses, serious malformation and stunting of the crop plants result. This abnormal growth in the crop plants results in loss of crop yield. Previous attempts to overcome this problem involves the treatment of the crop seed with certain antagonistic agents prior to planting, see U.S. Pat. Nos. 3,131,509 and 3,564,768. These antagonistic agents have not been notably successful. The aforementioned patent specifically exemplifies the treatment of seeds employing compounds of a different chemical class not suggestive of the present invention.

DESCRIPTION OF THE INVENTION

It has been discovered that plants can be protected against injury by various herbicides, for example, the thiocarbamate-type herbicides, alone or mixed with other herbicidal compounds and/or the tolerance of the plants can be substantially increased to the active compounds of the above-noted U.S. patents by adding to the soil an antidote compound corresponding to the following formula

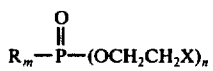

wherein R is lower alkoxy, haloalkyl or haloalkoxy, X is chlorine or bromine, $n$ is an integer from 1 to 3, inclusive, $m$ is 0 or an integer 1 or 2, provided that $n + m$ is 3. More preferably, X is bromine.

In the description of the phosphorus-containing compounds useful in the herbicidal antidote method of this invention, the following embodiments are intended for the various groups. The terms lower alkoxy, haloalkyl and haloalkoxy preferably includes those members, including straight chain and branched chain, having from 1 to 6 carbon atoms, inclusive, for example methoxy, ethoxy, n-propoxy, isopropoxy, n-butoxy, n-butyl, sec.-butoxy, tertiary-butoxy, n-pentoxy, isopentoxy, n-hexoxy, isohexoxy and the like; and as further examples, 2-bromoethyl, 1,2-dibromoethyl, 2,2,2-tribromoethyl, 3-chloropropyl, 3,4-dichlorobutyl, fluoromethyl, fluorochloroethyl, 1-fluorobutyl, 1-bromobutyl, 1,1,1-trichloroethyl, 2-chlorohexyl, and the corresponding haloalkoxy groups. The term halo preferably refers to fluoro, chloro and bromo substitutions as mono, di, tri and tetra substitutions. Halo also is intended to relate to mixed halogen substitutions, such as in dichloromonofluoromethyl and the like.

As an alternative mode of action, the compounds of this invention may interfere with the normal herbicidal action of the thiocarbamate-type and other herbicides to render them selective in their action. Whichever mode of action is present, the corresponding beneficial and desirable effect is the continued herbicidal effect of the thiocarbamate with the accompanying decreased herbicidal effect on desired crop species. This advantage and utility will become more apparent hereinafter.

Therefore, the terms herbicide, antidote or antidotal amount, is meant to describe that effect which tends to counteract the normal injurious herbicidal response that the herbicide might otherwise produce. Whether it is to be termed a remedy, interferant, protectant, or the like, will depend upon the exact mode of action. The mode of action is varied, but the counteracting effect, which is desirable, is the result of the method of treating the soil in which a crop is planted or the treatment of the seed with the antidote prior to planting in treated soil. Hitherto, there have been no systems which have been satisfactory for this purpose.

The compounds of this invention represented by the above formula can be prepared by several different procedures depending upon the starting materials.

In general, the compounds which act as herbicide antidotes within the scope of the instant invention can be prepared by the reaction of an appropriate halogen-containing alcohol and substituted phosphonochloridate or dichloridate. Wherein $m$ is 0 and $n$ is 3, the reaction is between the halogen-containing alcohol and phosphorus oxychloride, preferably in the presence of a hydrogen chloride acceptor such as pyridine or the like. An inert solvent can be used to facilitate the reaction and aid in the work-up procedure, for example, benzene. After completion of the selected reaction, the product is conveniently isolated by conventional work-up techniques.

The following examples, which are illustrative of the preparation and compounds useful in the instant invention, should not be construed as limiting examples, variations and modifications thereof will be apparent to one having ordinary skill in the art.

EXAMPLE I

Preparation of Tris-(2-bromoethyl)phosphate

A solution of 2.7 ml. (0.033 M) phosphorus oxychloride and 30 ml. benzene was added to a solution of 7.1 ml. (0.10 M) 2-bromoethanol, 8.1 ml. (0.10 M) pyridine and 70 ml. benzene. The addition was over a period of 15 minutes at a temperature of 15°-20° C. with stirring and necessary cooling. The reaction mixture was stirred at room temperature for 2 hours. The reaction mixture was washed with 100 ml. of water, separated and the organic portion dried over anhydrous magnesium sulfate. The solvent was evaporated in vacuo to yield an oil that was filtered through a small amount of dicalite. There was obtained 8.3 g. of the title compound, $n_D^{30} = 1.5162$.

EXAMPLE II

Preparation of O,O-di-2-bromoethyl chloromethylphosphonate

Chloromethyl phosphorodichloride (8.35 g., 0.05 mole) and 2-bromoethanol (12.5 g., 0.1 mole) were mixed together and stirred. An exothermic reaction took place. The mixture was stirred for 1¼ hours with heating. The resultant hydrogen chloride gas was removed by vacuum while heating with a hot water bath. When the reaction was complete, there was obtained 15.1 g. of the title compound $n_D^{30} = 1.5120$.

The compounds of the present invention and their preparation are more particularly illustrated by the following table. Following is a table of compounds which are prepared according to the procedures described herein. Compound numbers have been assigned to them and are used for identification throughout the balance of the specification.

TABLE I $$R_m-\overset{O}{\underset{\|}{P}}-(OCH_2CH_2X)_n$$

| COMPOUND NUMBER | R | m | X | n | $n_D^{30}$ |
|---|---|---|---|---|---|
| 1 | ClCH2 | 1 | Br | 2 | 1.5120 |
| 2 | C₂H₅O | 1 | Br | 2 | 1.4742 |
| 3 | — | 0 | Br | 3 | 1.5162 |
| 4 | ClCH2 | 1 | Cl | 2 | 1.4820 |

The compounds of this invention were employed in effective herbicidal antidote compositions comprising thiocarbamates in combination with antidote compounds described hereinabove.

Corn Seed Treatment Test

Small flats were filled with Felton loamy sand soil. Soil incorporated herbicides were applied at this time. The soil from each flat was placed into a 5-gallon cement mixer where the soil was mixed as the herbicides were applied using a predetermined amount of a stock solution containing 936 mg. of 75.5% active ingredient to 100 ml. of water. One ml. of stock solution was applied to the soil in a volumetric pipet for each pound of herbicide desired. One ml. of stock solution contained 7 mg. of herbicide which equals one pound per acre when applied to the soil in the flats. After the herbicide incorporation, the soil was placed back into the flats.

Flats of herbicide-treated and untreated soil were then ready to be planted. A pint sample of soil was removed from each flat and placed next to each flat for later use in covering up the seeds. The soil was leveled and rows one-half inch deep were made for planting seeds. Alternating rows of treated and untreated crop seeds were sown. In each test, six PAG 344T or DeKalb XL374 field corn seeds were planted in each row. Rows are approximately 1¼ inches apart in the flat. Seeds were treated by placing 50 mg. of the antidote compound with 10 grams of corn seed (0.5% w/w) in a suitable container and shaking them until the seeds were uniformly covered with the compound. Antidote compounds were also applied as liquid slurries and powders or dusts. In some cases, acetone was used to dissolve powdered or solid compounds so they could be more effectively applied to the seeds.

After the flats were seeded, they were covered with the 1 pint of soil which had been removed just prior to planting. Flats were placed on greenhouse benches where temperatures ranged from 70°-90° F. Flats were watered by sprinkling as needed to assure good plant growth. Percent control ratings were taken two and four weeks after the treatments were applied.

In each test, the herbicide was applied alone, in combination with the seed protectant, and the seed protectant was applied alone to check for phytotoxicity. The untreated adjacent row was employed to observe any beneficial lateral movement of the antidote compound through the soil. The degree of the effect was noted by comparison with the control. The results of these tests are tabulated in Table II.

TABLE II

Per Cent Injury to Corn from EPTC*
Seed Treatment Test

| | Per Cent Injury | | |
|---|---|---|---|
| | Treated Seed (0.5% w/w) | | Untreated Seed |
| COMPOUND NUMBER | 2 weeks | 4 weeks | Adjacent Row |
| 1 | 20 | 40 | 98 |
| 2 | 20 | 20 | 75 |
| 3 | 20 | 20 | 98 |
| 4 | 70 | 80 | 98 |

*EPTC = S-ethyl dipropylthiocarbamate 6E: 6 lb/Acre pre-plant incorporated

Tank Mix Application

Stock solutions of EPTC 6E (S-ethyl dipropylthiocarbamate) and SUTAN 6E (S-ethyl diisobutylthiocarbamate) were prepared as follows. For an equivalent of 6 lb/A. of EPTC, 304 mg. were dissolved in 50 ml. of water. For an equivalent of 12 lb/A. of SUTAN, 608 mg. were dissolved in 50 ml. of water.

The antidote solutions equivalent to 10 lb/A. were prepared by dissolving 380 mg. in 20 ml. of water. Two milliliters of this stock solution was used in each flat, thereby achieving 10 lb/A. (38 mg.) of antidote compound.

Tank-mix procedure

To 5 ml. of herbicide stock solution in a bottle was added 2 ml. of stock antidote solution. This was shaken well. The entire contents (7 ml.) was injected into the soil from a flat, while incorporation was accomplished using a five gallon rotary mixer. After incorporation, soil was replaced in the flat.

Seeding plans in each flat, including a control flat, where only herbicide was applied, were as follows:
Wild oats — WO
DeKalb XL-44 — Corn
Foxtail — FT
Watergrass — WG
Crabgrass — CG The results four weeks after planting in the treated soil are given in the following table.

TABLE III

| | Per Cent Injury | | | | |
|---|---|---|---|---|---|
| HERBICIDE ANTIDOTE* Pre-plant incorporation Treatment | WO | DeKalb XL-44 Corn | FT | WG | CG |
| EPTC 6E/ — | 100 | 95 | 98 | 100 | 99 |
| EPTC 6E/Cmpd. No. 1 | 100 | 0 | 98 | 100 | 99 |
| EPTC 6E/Cmpd. No. 2 | 100 | 50 | 98 | 100 | 99 |
| EPTC 6E/Cmpd. No. 3 | 100 | 70 | 98 | 100 | 99 |
| EPTC 6E/Cmpd. No. 4 | 100 | 95 | 98 | 100 | 99 |
| SUTAN 6E/ — | 100 | 70 | 98 | 100 | 99 |
| SUTAN 6E/Cmpd. No. 1 | 100 | 0 | 98 | 100 | 99 |
| SUTAN 6E/Cmpd. No. 2 | 100 | 0 | 98 | 100 | 99 |
| SUTAN 6E/Cmpd. No. 3 | 100 | 0 | 98 | 100 | 99 |

TABLE III-continued

| HERBICIDE ANTIDOTE* Pre-plant incorpora- tion Treatment | Per Cent Injury | | | | |
|---|---|---|---|---|---|
| | WO | DeKalb XL-44 Corn | FT | WG | CG |
| SUTAN 6E/Cmpd. No. 4 | 100 | 50 | 98 | 100 | 99 |

*Identification can be found in Table I, supra

The antidote compounds and compositions of the present invention can be used in any convenient form. Thus, the antidote compounds can be formulated into emulsifiable liquids, emusifiable concentrates, liquid, wettable powder, powders, granular or any other convenient form. In its preferred form, a non-phytotoxic quantity of an herbicidal antidote compound is admixed with a selected herbicide and incorporated into the soil prior to or after planting the seed. It is to be understood, however, that the herbicides can be incorporated into the soil and thereafter the antidote compound can be incorporated into the soil. Moreover, the crop seed itself can be treated with a non-phytotoxic quantity of the compound and planted into the soil which has been treated with herbicides, or untreated with the herbicide and subsequently treated with the herbicide. The addition of the antidote compound does not affect the herbicidal activity of the herbicides.

The amount of antidote compound present can range between about 0.001 to about 15 parts by weight of antidote compound described herein per each part by weight of herbicide. The exact amount of antidote compound will usually be determined on economic ratios for the most effective amount usable. It is understood that a non-phytotoxic quantity of antidote compound will be employed in the herbicidal compositions described herein.

The herbicides indicated in the tables and elsewhere are used at rates which produce effective control of undesirable vegetation. The rates are within the recommended amounts set forth by the supplier. Therefore, the weed control in each instance is commercially acceptable within the desired or recommended amount.

It is clear that the classes of herbicidal agents described and illustrated herein are characterized as effective herbicides exhibiting such activity. The degree of this herbicidal activity varies among specific compounds and among combinations of specific compounds within the classes. Similarly, the degree of activity to some extent varies among the species of plants to which a specific herbicidal compound or combination may be applied. Thus, selection of a specific herbicidal compound or combination to control undesirable plant species readily may be made. Within the present invention, prevention of injury to a desired crop species in the presence of a specific compound or combination may be achieved. The beneficial plant species which can be protected by this method is not intended to be limited by the specific crops employed in the examples.

The herbicidal compounds employed in the utility of this invention are active herbicides of a general type. That is, the members of the classes are herbicidally effective against a wide range of plant species with some degree of discrimination between desirable and undesirable species. The method of controlling vegetation comprises applying an herbicidally effective amount of the hereindescribed herbicidal compounds to the area or plant locus where control is desired. The compositions as set forth in this invention include those wherein the preferred active herbicidal compound is selected from S-ethyl dipropylthiocarbamate, S-ethyl diisobutyl thiocarbamate, S-propyl dipropylthiocarbamate, S-2,3,3-trichloroallyl-diisopropyl thiocarbamate, S-ethyl cyclohexyl ethyl thiocarbamate, 2-chloro-2',6"-diethyl-N-(methoxymethyl)acetanilide, S-ethyl hexahydro-1H-azepine-1-carbothioate, 2-chloro-N-isopropylacetanilide, N,N-diallyl-2-chloroacetamide, S-4-chlorobenzyl diethyl thiocarbamate, 2-chloro-4-ethylamino-6-isopropylamino-s-triazine, 2-chloro-4,6-bis(ethylamino)-s-triazine, 2(4-chloro-6-ethylamine-s-triazine-2-yl-amino)-2-methylpropionitrile, 2-chloro-4-cyclopropylamino-6-isopropylamino-s-triazine, 2,4-dichlorophenozyacetic acid, its esters and salts, and 3-(3,4-dichlorophenyl)-1,1-dimethylurea and combinations thereof.

An herbicide as used herein means a compound which controls or modifies the growth of vegetation or plants. Such controlling or modifying effects include all deviations from natural development; for example, killing, retardation, defoliation, desiccation, regulation, stunting, tillering, stimulation, dwarfing and the like. By "plants" it is meant germinant seeds, emerging seedlings, and established vegetation, including the roots and above-ground portions.

What is claimed is:

1. A herbicidal composition comprising an active herbicidal thiocarbamate compound selected from S-ethyl dipropyl thiocarbamate, S-ethyl diisobutyl thiocarbamate, S-propyl dipropyl thiocarbamate, S-2,3,3-trichloroallyl-diisopropyl thiocarbamate, S-ethyl cyclohexyl ethyl thiocarbamate, S-ethyl hexahydro-1H-azepine-1-carbothioate and S-4-chlorobenzyl diethyl thiocarbamate and an antidotally effective amount of an antidote compound corresponding to the formula

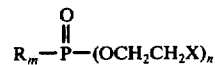

$$R_m-\overset{O}{\underset{\|}{P}}-(OCH_2CH_2X)_n$$

wherein R is lower alkoxy having from 1 to 6 carbon atoms, inclusive, haloalkyl having from 1 to 6 carbon atoms, inclusive, and wherein halo refers to fluoro, chloro and bromo substitutions, or haloalkoxy having from 1 to 6 carbon atoms, inclusive and wherein halo refers to fluoro, chloro and bromo substitutions, X is chlorine or bromine, n is an integer from 1 to 3, inclusive, m is 0 or an integer 1 or 2, provided that $n + m$ is 3.

2. The composition as set forth in claim 1 wherein said antidote compound is present in an amount ranging between about 0.001 to about 15 parts by weight for each part by weight of the herbicide compound.

3. The composition according to claim 1 in which R is haloalkyl, X is bromine, m is 1 and n is 2.

4. The composition according to claim 3 in which R is chloromethyl.

5. The composition according to claim 1 in which R is haloalkyl, X is chlorine, m is 1 and n is 2.

6. The composition according to claim 5 in which R is chloromethyl.

7. The composition according to claim 1 in which R is alkoxy, X is bromine, m is 1 and n is 2.

8. The composition according to claim 7 in which R is ethoxy.

9. The composition according to claim 1 in which m is 0, X is bromine and n is 3.

10. A method of selectively controlling weed pests in the presence of crops comprising applying to the habitat thereof an herbicidally effective amount of the composition as set forth in claim 1.

11. The composition as set forth in claim 1 wherein said active herbicidal compound is selected from S-ethyl dipropyl-thiocarbamate, S-ethyl diisobutyl thiocarbamate and S-propyl dipropyl thiocarbamate.

12. The method of selectively controlling weed pests in the presence of crops comprising applying to the habitat thereof an herbicidally effective amount of the composition as set forth in claim 11.

13. The method of protecting corn crop from injury due to a thiocarbamate herbicide, selected from S-ethyl dipropyl thiocarbamate, S-ethyl diisobutyl thiocarbamate, S-propyl dipropyl thiocarbamate, S-2,3,3-trichloroally-diisopropyl thiocarbamate, S-ethyl cyclohexyl ethyl thiocarbamate, S-ethyl hexahydro-1H-azepine-1-carbothioate and S-4-chlorobenzyl diethyl thiocarbamate, comprising applying to the corn seed prior to planting a non-phytotoxic antidotally effective amount of a compound corresponding to the formula

wherein R is lower alkoxy having from 1 to 6 carbon atoms, inclusive, haloalkyl having from 1 to 6 carbon atoms, inclusive, and wherein halo refers to fluoro, chloro and bromo substitutions, haloalkoxy having from 1 to 6 carbon atoms, inclusive, and wherein halo refers to fluoro, chloro and bromo substitutions, X is chlorine or bromine, $n$ is an integer from 1 to 3, inclusive, $m$ is 0 or an integer 1 or 2, provided that $n + m$ is 3.

14. The method of claim 13 in which the thiocarbamate herbicide is selected from the group S-ethyl dipropylthiocarbamate, S-ethyl diisobutyl thiocarbamate, S-propyl dipropyl thiocarbamate, S-2,3,3-trichloroallyl-diisopropyl thiocarbamate, S-ethyl cyclohexyl ethyl thiocarbamate, S-ethyl hexahydro-1H-azepine-1-carbothioate, S-4-chlorobenzyl diethyl thiocarbamate, and mixtures thereof.

15. The method of protecting corn crop from injury due to a thiocarbamate herbicide selected from S-ethyl dipropyl thiocarbamate and S-ethyl diisobutyl thiocarbamate, comprising preplant incorporation in the soil in which said corn crops is to be planted, a non-phytotoxic antidotally effective amount of a compound corresponding to the formula

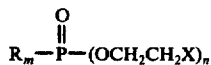

wherein R is lower alkoxy having from 1 to 6 carbon atoms, inclusive, haloalkyl having from 1 to 6 carbon atoms, inclusive and wherein halo refers to fluoro, chloro and bromo substitutions, haloalkoxy having from 1 to 6 carbon atoms, inclusive and wherein halo refers to fluoro, chloro and bromo substitutions, X is chlorine or bromine, $n$ is an integer from 1 to 3, inclusive, $m$ is 0 or an integer 1 or 2, provided that $n + m$ is 3.

16. An herbicidal composition according to claim 1 in which X is bromine.

17. The method of claim 13 in which X is bromine.

18. The method of claim 15 in which X is bromine.

* * * * *